(12) United States Patent
Grinberg et al.

(10) Patent No.: US 7,235,104 B2
(45) Date of Patent: Jun. 26, 2007

(54) METHOD OF PROTECTING AND LUBRICATING BEARING SURFACES OF AN ARTIFICIAL DISC

(75) Inventors: Alexander Grinberg, Newton, MA (US); Douglas Hester, Raynham, MA (US); Edward Zalenski, Lakeville, MA (US)

(73) Assignee: Depuy Spine, Inc., Raynham, MA (US)

( * ) Notice: Subject to any disclaimer, the term of this patent is extended or adjusted under 35 U.S.C. 154(b) by 230 days.

(21) Appl. No.: 10/992,981

(22) Filed: Nov. 19, 2004

(65) Prior Publication Data

US 2006/0111784 A1    May 25, 2006

(51) Int. Cl.
A61F 2/44    (2006.01)

(52) U.S. Cl. .................................................. 623/17.14
(58) Field of Classification Search ............. 623/17.14, 623/17.15
See application file for complete search history.

(56) References Cited

U.S. PATENT DOCUMENTS

| 6,113,637 | A | 9/2000 | Gill et al. |
| 2002/0035400 | A1 | 3/2002 | Bryan |
| 2004/0133278 | A1 | 7/2004 | Marino |
| 2004/0193273 | A1 | 9/2004 | Huang |

*Primary Examiner*—David H. Willse
*Assistant Examiner*—Javier G. Blanco

(57) ABSTRACT

An intervertebral motion disc having a temporary liner disposed at an articulation interface.

1 Claim, 6 Drawing Sheets

METHOD OF PROTECTING AND LUBRICATING BEARING SURFACES OF AN ARTIFICIAL DISC

BACKGROUND OF THE INVENTION

The leading cause of neck pain arises from rupture or degeneration of cervical intervertebral discs. Pain in the upper extremities may be caused by compression of spinal nerve roots by a bulging disc, while neck pain may be caused by collapse of the disc and by the adverse effects of bearing weight through a damaged, unstable vertebral joint. One conventional method of managing these problems is to remove the problematic disc and replace it with a prosthetic disc that allows for the natural motion between the adjacent vertebrae ("a motion disc").

U.S. Pat. No. 6,113,637 ("Gill") discloses a motion disc having a ball and socket articulation, wherein the trough of the socket has a flat portion. The ball and socket geometry provides pivotal motion while the flat portion of the trough allows the ball to slide, thereby providing some translation motion. Gill further discloses a method of linering the motion disc whereby an linering device engages the ball and socket components to fix the spatial relationship between the components. The components are then linered into the disc space in this fixed spatial relationship. Therefore, during the entire insertion procedure, the original spatial relationship may be maintained.

SUMMARY OF THE INVENTION

The present inventors have developed an invention wherein a temporary protective liner is provided between the ball and socket components of the artificial disc. This liner prevents the bearings surfaces of the respective components from bearing and/or wearing against each other during pre-operative handling of the disc. After a holding device secures the artificial disc during the implantation procedure, the protective liner is removed, thereby creating a gap between the bearing surfaces of the ball and socket components in the space formerly occupied by the liner. This gap advantageously allows for the intra-operative interposition of a lubricant between the bearing surfaces. The lubricant advantageously eliminates or reduces dry contact and friction between the bearing surfaces during the initial use of the motion disc.

Therefore, in accordance with the present invention, there is provided an intervertebral motion disc comprising:
a) a first component comprising:
  i) an outer surface adapted to mate with a first vertebral body,
  ii) an inner surface having a first articulation surface suitable for supporting articulation motion thereon, and
  iii) a body portion connecting the inner and outer surfaces, and
b) a second component comprising:
  i) a second articulation surface suitable for supporting articulation motion thereon and defining an articulation interface with the first articulation surface, and
c) a protective liner disposed between the first and second articulation interfaces.

Also in accordance with the present invention, there is provided an intervertebral motion disc comprising:
a) a first component comprising:
  i) an outer surface adapted to mate with a vertebral body,
  ii) an inner surface having a first articulation surface suitable for supporting articulation motion thereon, and
  iii) a body portion connecting the inner and outer surfaces, and
b) a second component comprising:
  i) a second articulation surface suitable for supporting articulation motion thereon and defining an articulation interface with the first articulation surface, and
c) a flowable lubricant disposed between the first and second articulation interfaces.

Also in accordance with the present invention, there is provided a method of protecting an articulation interface, comprising the steps of:
a) providing a motion disc comprising,
  a first component comprising:
    i) an outer surface adapted to mate with a first vertebral body,
    ii) an inner surface having a first articulation surface suitable for supporting articulation motion thereon, and
    iii) a body portion connecting the inner and outer surfaces, and
  a second component comprising:
    i) a second articulation surface suitable for supporting articulation motion thereon and defining an articulation interface with the first articulation surface, and
    a protective liner disposed between the first and second articulation interfaces, and
b) removing the liner to form a gap between the articulation surfaces, and
c) inserting the disc into a disc space.

DESCRIPTION OF THE FIGURES

FIG. 1b discloses a perspective view of a protective liner disposed upon the lower component of the cervical motion disc of FIG. 1a.

DETAILED DESCRIPTION

Figure 1A:
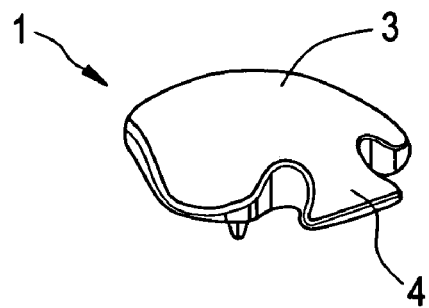
FIG. 1a discloses a perspective view of a lower component of a cervical motion disc.
Figure 1B:
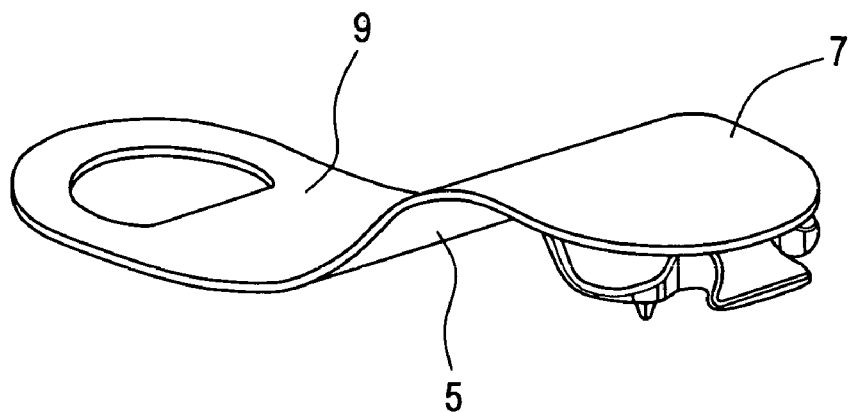
Figure 1C:
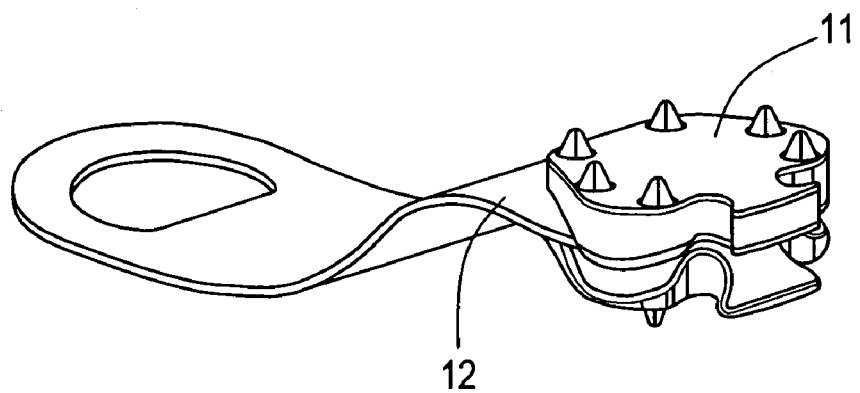
FIG. 1c discloses a perspective view of the protective liner of FIG. 1b disposed between an upper component and a lower component of the cervical motion disc.

Now referring to FIGS. 1a–1c, there is provided a process of preparing the motion disc of the present invention during packaging. FIG. 1a discloses a first step of providing a first disc component 1 of a cervical motion disc having a ball-type articulation surface 3 and proximal engagement portion 4.

In FIG. 1b, there is provided a second step in which a lower face of protective liner 5 is laid upon the ball-type articulation surface 3 of the first disc component such that a substantial portion of the liner does not contact the articulation surface, thereby defining a contact portion 7 and non-contact portion 9 of the liner.

In FIG. 1c, there is provided a third step wherein a second disc component 11 having a socket-type articulation surface (not shown) is laid upon the upper face 12 of the liner so that a non-contact portion of the liner lies outside the articulation interface. Thus, the protective liner is located between the highly polished articulation surfaces of the disc and prevents them from wearing or scratching each other before implantation of the disc.

Figure 2A:
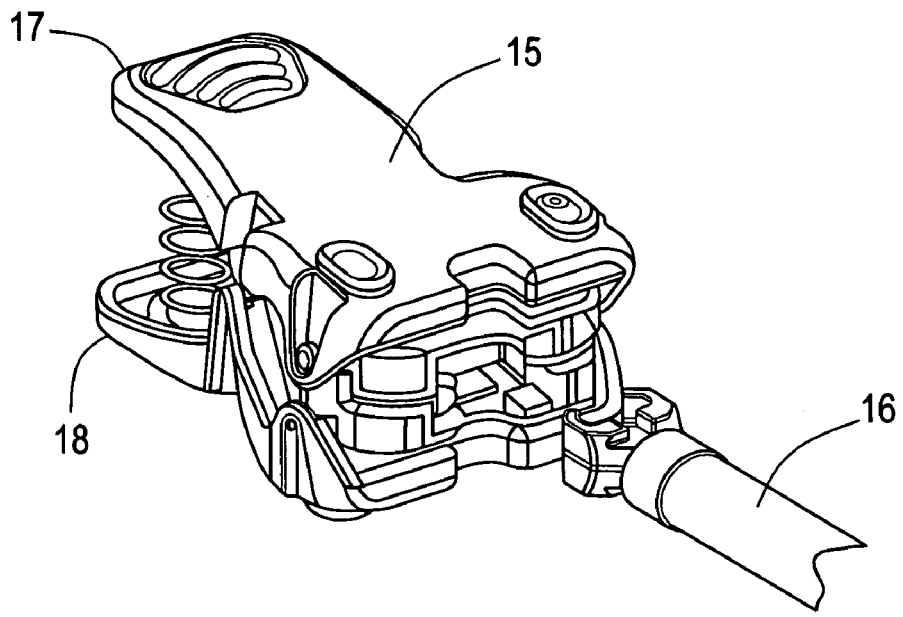
FIG. 2a discloses a perspective view of a motion disc of the present invention held within a disc clip.

During the pre-operative transportation and handling of the disc, it is desirable to interpose the protective liner between the disc components. Now referring to FIGS. 2a and 2b, the disposition of the protective liner between the disc components may be achieved by holding them in a clip device 15 having opposed handles 17, 18. Preferred clip devices are shown in U.S. patent application Ser. No. 10/750,173, filed Dec. 31, 2003 (Zalenski et al.), the specification of which is incorporated by reference in its entirety.

Figure 2B:
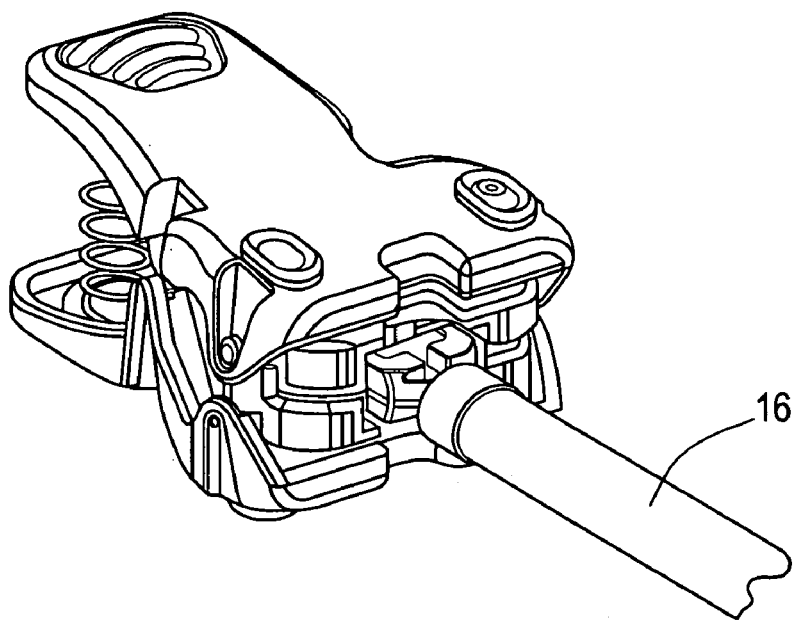
FIG. 2b discloses a perspective view of the motion disc of FIG. 2a being secured by a holding instrument.
Figure 2C:
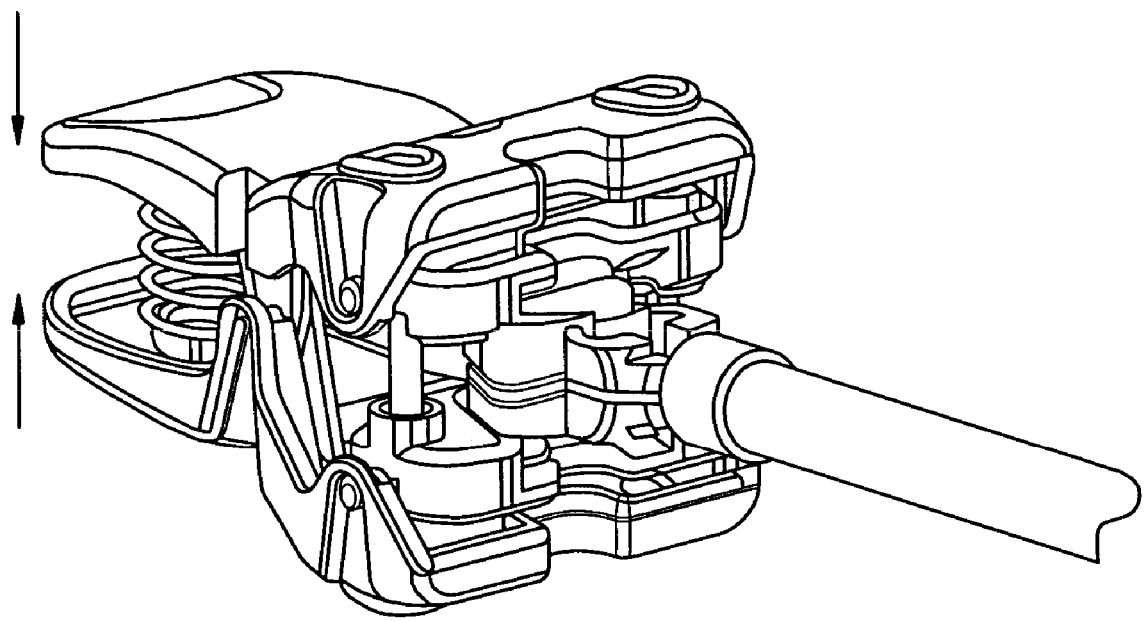
FIG. 2c discloses the squeezing of the disc clip handles of FIG. 2b.
Figure 2D:
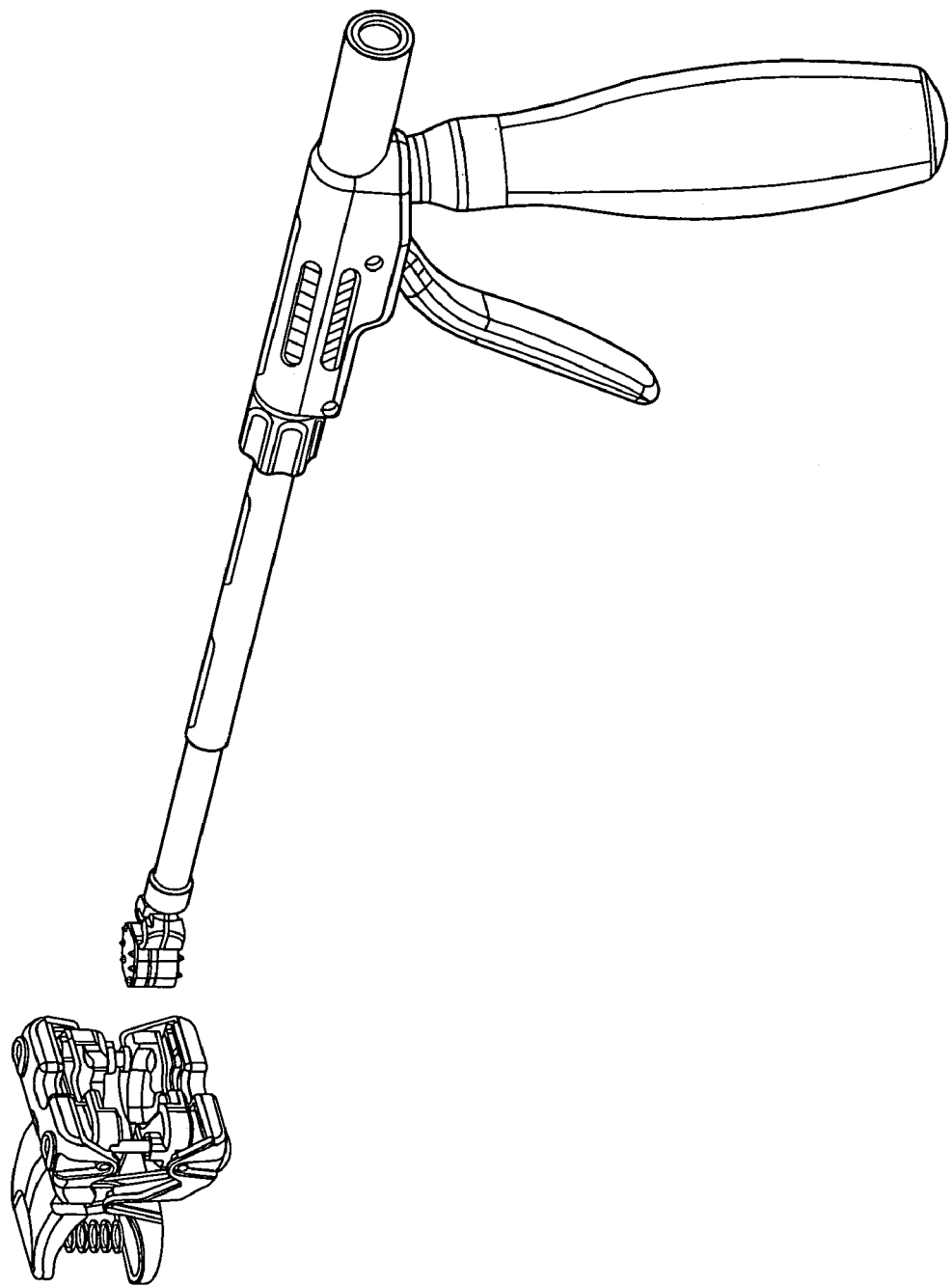
FIG. 2d discloses the withdrawal of the disc of FIG. 2c from the disc clip by the holding instrument.

When the patient is ready to receive the motion disc, a holding instrument 16 engages the proximal engagement portion 4 of the disc (as shown in FIG. 2b). Preferred holding instruments are shown in U.S. patent application Ser. No. 10/750,173, filed Dec. 31, 2003 (Zalenski et al.), the specification of which is incorporated by reference in its entirety. The opposed handles 17,18 of the clip device are then squeezed together (as shown in FIG. 2c) and the holding device is pulled away from the clip device, thereby releasing the disc from the clip device to the holding instrument (as shown in FIG. 2d).

In some embodiments, the liner is not secured to the disc clip and so may be manually removed from the articulation interface after the disc has been removed from the disc clip.

Figure 3A:
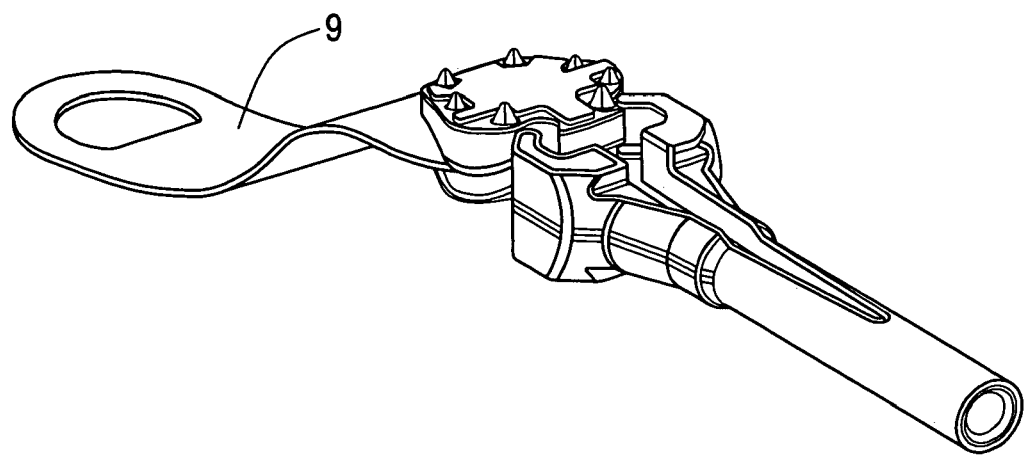
FIGS. 3a–b disclose the removal of a secured liner from the disc.
Figure 3B:
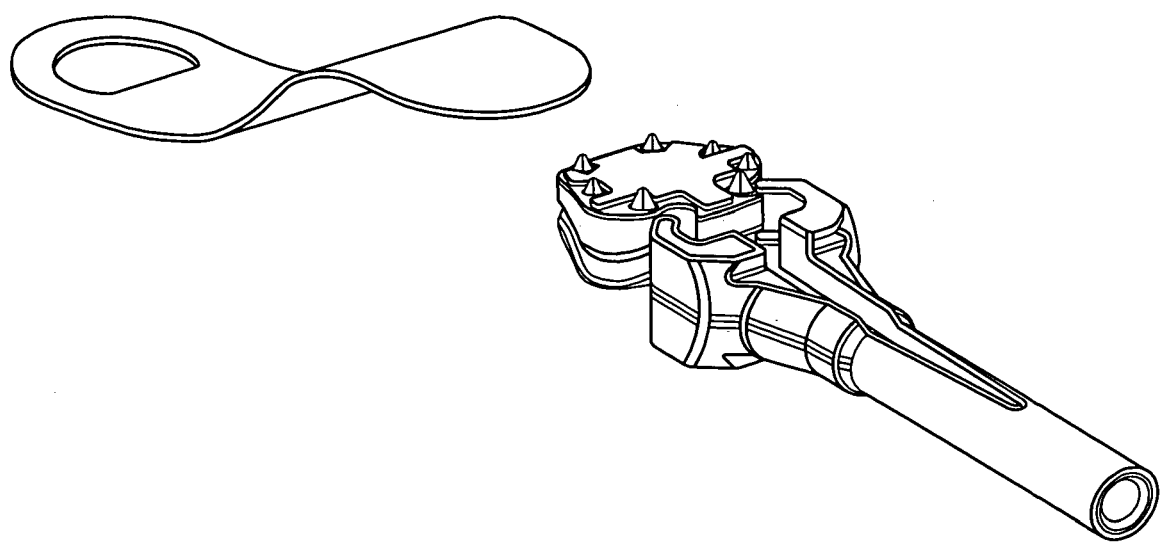

In other embodiments, and now referring to FIG. 3a, the non-contact portion 9 of the protective liner is secured to the disc clip by a securing means (not shown), such as a mechanical means or an adhesive means. Because it is secured to the disc clip in this embodiment, the liner is removed from between the bearing surfaces during removal of the disc from the disc clip, as shown in FIG. 3b.

Figure 4A:
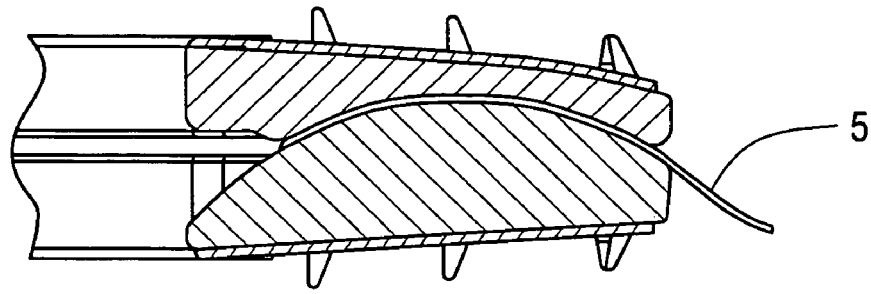
FIGS. 4a–b disclose a cross-section view of there creation of a gap caused by removal of the liner.
Figure 4B:
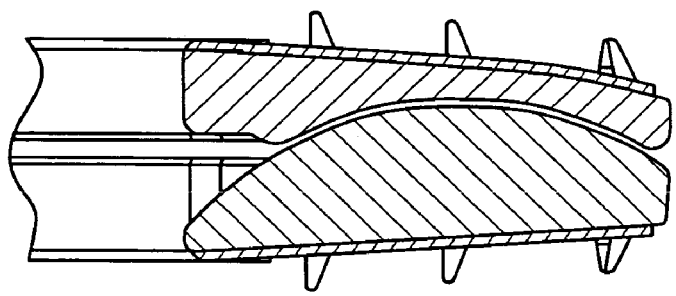

Now referring to FIG. 4a, there is provided a cross-section of the disc having the liner disposed therein and being held by the holding instrument. Now referring to FIG. 4b, when the holding instrument withdraws the disc from the disc clip and the liner is withdrawn from the articulation interface, a gap 21 is created at the articulation interface.

This gap provides a space into which a flowable lubricant can be introduced to lubricate the sensitive articulation surfaces. This lubricant will prevent the articulation interface from experiencing high friction during the initial bearing period after implantation. As the disc articulates during normal use, it is contemplated that physiologic lubricating fluid will eventually replace the lubricant.

In some embodiments, the lubricant may be introduced into the gap by either a syringe injection or by dipping the disc into a lubricant bath.

In some embodiments, the lubricant may be saline. In other embodiments, the lubricant may be a physiologic fluid obtained from the patient.

Figure 4C:
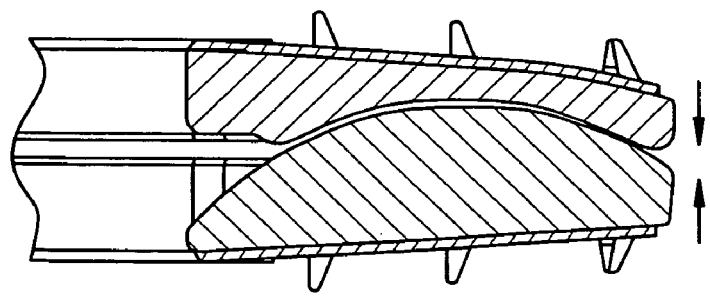
FIG. 4c discloses a cross-section view of the reduction and/or elimination of the gap caused by insertion of the disc into a disc space.

Now referring to FIG. 4c, during insertion of the posterior end 23 of the disc into the disc space, the physiologic compressive forces of the vertebral column are exerted upon the posterior teeth of the disc. These forces reduce or eliminate the gap at the posterior end of the disc, thereby squeezing some of the lubricant from the gap. However, despite the reduction in the gap, a thin film of lubricant will likely remain between the articulation surfaces to reduce the friction between the articulation surfaces during the initial wear phases on the device.

Preferably, the liner is made of a flexible material that can conform to curved articulation surfaces. The liner material also preferably is made of a soft material that will not scratch the bearing surfaces. Accordingly, the liner preferably has a hardness no more than $1/100$th the hardness of an articulation surface. Preferably, the liner is made of a soft, flexible polymer, such as Tyvek™.

In some embodiments, the liner has a thickness of between 0.1 and 0.5 mm. In this thickness range, the liner has both the flexibility to conform to curved articulation surfaces and the strength to bear minor pre-insertion loading without tearing.

Preferably, the length of one face of the liner is greater than the corresponding length of the articulation surface upon which it bears. This requirement allows the liner to have a non-contact portion that can be pulled when the liner needs to be removed.

Also preferably, it is preferred that the opposed faces of the liner each define an area that is at least $1/4$ the area of the articulation surface upon which it rests. The requirement helps reduce the likelihood of pre-operative scratching between the articulation surfaces.

The motion disc component of the present invention can be any prosthetic capable of restoring the natural motions of the intervertebral disc. In preferred embodiments, the motion disc is selected from the group consisting of an articulating disc, a cushion disc and a spring-based disc.

In some embodiments, the general structure of the articulating motion disc is a two piece design and comprises:
 a) a first prosthetic vertebral endplate comprising:
  i) an outer surface adapted to mate with a first vertebral body,
  ii) an inner surface having a first articulation surface,
  iii) a body portion connecting the inner and outer surfaces,
 b) a second prosthetic vertebral endplate comprising:
  i) an outer surface adapted to mate with a second vertebral body, and
  ii) an inner surface comprising a second articulation surface,
 wherein the first and second articulation surfaces are oriented produce an articulation interface.

Preferably, the articulation surfaces form partial spheres.

In these two-piece embodiments, the liner is inserted between the articulation surfaces at the articulation interface.

In some embodiments, the general structure of the articulating motion disc is three-piece and comprises:
 a) a first prosthetic vertebral endplate comprising:
  i) an outer surface adapted to mate with a first vertebral body,
  ii) an inner surface having a first articulation surface,
  iii) a body portion connecting the inner and outer surfaces,
 b) a second prosthetic vertebral endplate comprising:
  i) an outer surface adapted to mate with a second vertebral body, and
  ii) an inner surface comprising a first articulation surface, c) a core member comprising:
   i) a first articulation surface adapted for articulation with the first articulation surface of the first endplate, and
   ii) a second articulation surface adapted for articulation with the first articulation surface of the second endplate, wherein the core member is oriented to produce a first articulation interface between the first articulation surface of the first endplate and the first articulation surface of the core member, and a second articulation interface between the first articulation surface of the second endplate and the second articulation surface of the core member.

Preferred articulating motion devices are disclosed in U.S. Pat. Nos. 5,556,431 and 5,674,296, the specifications of which are incorporated by reference in their entireties.

The motion discs of the present invention can be adapted for use any of the lumbar, thoracic or cervical spine regions. In some embodiments wherein the motion disc is adapted for use in the lumbar region, the three-piece design having a core is selected. In some embodiments wherein the motion disc is adapted for use in the cervical region, the two-piece design is selected.

We claim:
1. A method of protecting an articulation interface, comprising the steps of:
   a) providing a motion disc comprising,
      a first component comprising:
         i) an outer surface adapted to mate with a first vertebral body,
         ii) an inner surface having a first articulation surface suitable for supporting articulation motion thereon, and
         iii) a body portion connecting the inner and outer surfaces, and
      a second component comprising:
         i) a second articulation surface suitable for supporting articulation motion thereon and defining an articulation interface with the first articulation surface, and
      a protective liner disposed between the first and articulation surfaces at said interface,
   b) removing the liner to form a gap between the articulation surfaces,
   c) inserting the disc into a disc space, and
   d) applying a lubricant to the gap prior to inserting the disc into the disc space.

* * * * *